United States Patent [19]

Della Bianca

[11] 4,060,348

[45] Nov. 29, 1977

[54] ROLLER PUMP CARRYING OUT ALTERNATE PUMPING OPERATIONS, PARTICULARLY SUITED TO EXTRA-CORPOREAL BLOOD CIRCULATION

[75] Inventor: Luciano Della Bianca, Voghera, Italy

[73] Assignee: Bioengineering Research S.A., Luxembourg

[21] Appl. No.: 699,203

[22] Filed: June 23, 1976

[30] Foreign Application Priority Data

July 1, 1975 Italy ........................ 24991/75

[51] Int. Cl.[2] ............... F04B 43/08; F04B 43/12; F04B 45/06
[52] U.S. Cl. .......................... 417/475; 417/477
[58] Field of Search ............... 417/475, 476, 477; 128/214 F, DIG. 3, DIG. 12

[56] References Cited

U.S. PATENT DOCUMENTS

| 1,741,070 | 12/1929 | Oliveras | 417/477 |
|---|---|---|---|
| 2,909,125 | 10/1959 | Daniels | 417/477 |
| 3,039,442 | 6/1962 | Hornschuch et al. | 417/477 |
| 3,429,273 | 2/1969 | Jones | 417/477 |
| 3,737,251 | 6/1973 | Berman et al. | 417/477 |
| 3,876,340 | 4/1975 | Thomas | 417/475 |
| 3,985,134 | 10/1976 | Lissot et al. | 128/214 F |

*Primary Examiner*—Carlton R. Croyle
*Assistant Examiner*—Thomas I. Ross
*Attorney, Agent, or Firm*—Browdy and Neimark

[57] ABSTRACT

A rotary roller pump for carrying out sequential pumping of fluid in separate squeezable tubings comprises a stator and a rotor which is provided at opposite ends with rollers, for respective engagement with the tubings, and is so mounted that a gap is provided between an inwardly facing seating of the stator which part-surrounds the rotor, and the rollers for accommodating the tubings which are to be arranged substantially parallel to each other and so as to extend in the general circumferential direction. Each roller comprises two cylindrical and co-axial parts having different diameters such that, with the tubings so accommodated and arranged, the cylindrical part having the larger diameter engages one of the tubing placed between that cylindrical part and the inwardly facing seating in such manner as to exert a pumping action on that tubing when the rotor rotates, whereas the cylindrical part having the smaller diameter does not exert a pumping action on the remaining tubing.

7 Claims, 4 Drawing Figures

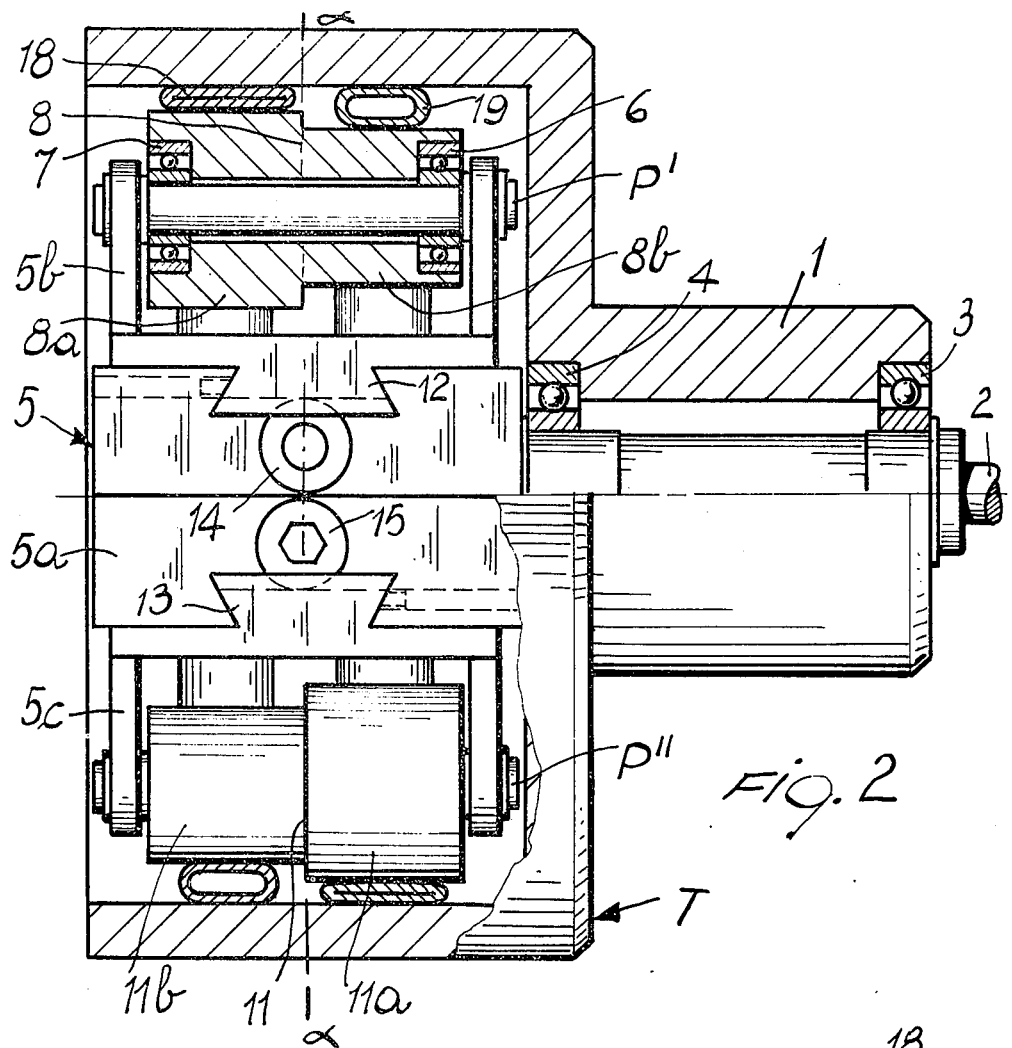
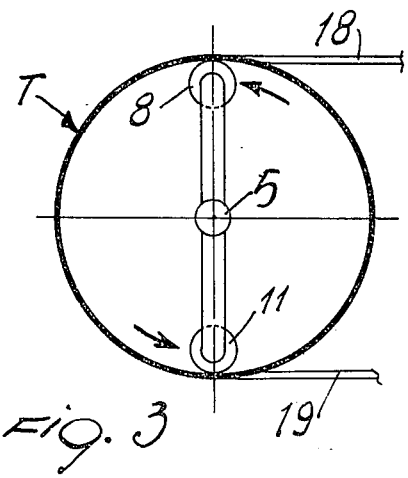
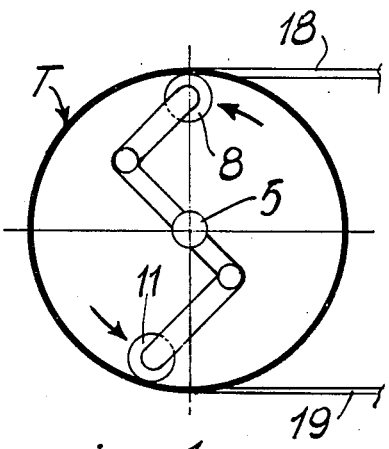

ROLLER PUMP CARRYING OUT ALTERNATE PUMPING OPERATIONS, PARTICULARLY SUITED TO EXTRA-CORPOREAL BLOOD CIRCULATION

BACKGROUND OF THE INVENTION

1. Field of the invention

This invention relates to a rotary roller pump for carrying out a sequential pumping of fluid in a plurality of separate squeezable tubings.

Although the rotary roller pump according to this invention can be advantageously used in technological applications in general, wherein it is desired to perform, by means of only one pump, sequential pumping operations on two or more separate tubings, this invention will be described by making specific reference to its applicatons in the medical field and particularly in the establishment of extra-corporeal blood circulation which is made necessary for instance during the dialysis and ultrafiltration of blood, and within the frame of various medical and surgical interventions and situations which require the use of the so-called "heart-lung machines" and similar devices.

2. Description of the prior art

Within the frame of the above mentioned medical and surgical situations, there is a frequent need to have at one's disposal some devices by means of which an alternate pumping on the hematic liquid conveyed along two separate and distinct tubings is accomplished (pumps for use in the boimedical field are e.g. disclosed in the U.S. Pat. Nos. 2,659,368; 2,705,493; and 3,045,601). For instance, when performing the dialysis and ultrafiltration of blood with the cannulation technique with a single needle and a Y-junction, in the extra-corporeal circuit which comprises a length of arterial line for transferring the blood to be purified from the patient's arterialised vein to the dialyzer, and a length of venous line for conveying the purified blood from the dialyzer to the arterialised vein, a double-pumping action is needed to ensure the required blood flow rate. Because the pumping operations on the arterial and venous lines of the circuit must alternate according to a preset time sequence, the use of two pumps or a double-head pump not only requires distinct driving means but also electronic synchronizing means for actuating the pumps or the pump heads according to the pre-established time sequence. This in turn does not only increase the complexity of the pumping devices with the attendant increase of the risk that breakdowns and interruptions may take place, but also weighs heavily on the manufacturing and maintenance costs of the units in which the above mentioned extra-corporeal circuits are used.

SUMMARY OF THE INVENTION

It is therefore an aim of this invention to provide a rotary roller pump of relatively simple construction, by means of which it is possible to perform alternate pumping operations on two separate and distinct tubings or lines.

According to the invention there is provided a rotary roller pump for carrying out sequential pumping of fluid in a plurality of separate squeezable tubings, the pump comprising a stator and a rotor which is provided at opposite lateral ends with rollers, for respective engagement with the said tubings, and is so mounted that a gap is provided between an inwardly facing seating of the stator, which seating part-surrounds the rotor, and said rollers for accommodating said tubings which are to be arranged substantially parallel to each other and so as to extend in the general circumferential direction, each roller comprising two cylindrical and co-axial parts having different diameters such that, with said tubings so accommodated and arranged, the cylindrical part having the larger diameter engages a respective said tubing between that cylindrical part and the inwardly facing seating in such manner as to exert a pumping action on that tubing when the rotor rotates whereas the cylindrical part having the smaller diameter does not exert a pumping action on the or each remaining tubing.

BRIEF DESCRIPTION OF THE DRAWINGS

FIG. 2 is a side, part cross-sectional and part cutaway view of the pump head along line II—II of FIG. 1;

FIG. 3 is an end view, corresponding to FIG. 1, showing, diagrammatically, the pump head where rollers of the pump are arranged in such a way that the beginning of the pumping step on one tubing coincides with the end of the pumping step on the other tubing; and FIG. 4 is an end view, corresponding to that in FIG. 3, but in which the rollers are arranged in such a way that the beginning of the pumping step on one tubing takes place before the end of the pumping step on the other tubing.

DESCRIPTION OF THE PREFERRED EMBODIMENTS

Figure 1:
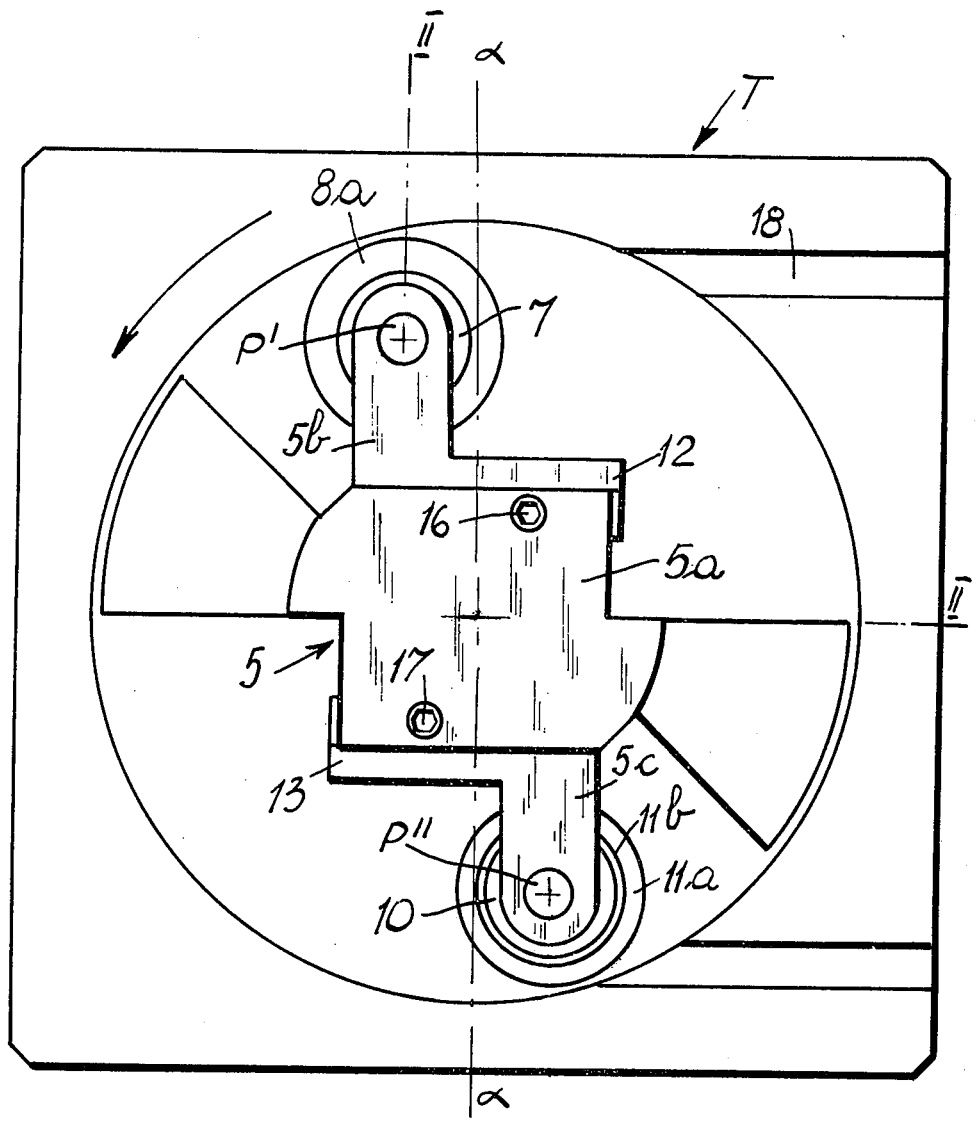
FIG. 1 is an end view of a pump head of one form of rotary roller pump in accordance with the invention.

With reference to the drawings, the roller pump, which is constructed to perform alternate pumping on two separate squeezable tubings, comprises a pump head which is generally designated by the reference letter T, the motor and other conventional accessories being not shown in the drawings for the sake of simplicity. Head T comprises a stator 1 provided with fixing stirrups (not shown) for securing the pump to a base (not shown). The stator 1 has a semi-cylindrical seating therein which faces inwardly towards the longitudinal axis of the pump. A shaft 2 is rotatably mounted in an axial position within the semi-cylindrical seating, the ends of the shaft being fitted in roller bearings 3, 4 housed in suitable recesses provided in the stator.

On shaft 2 is keyed a rotor 5, which comprises a central body 5a fixedly secured to the shaft 2, and removably mounted clevis-shaped elements 5b, 5c. A pivot P' extends between the arms of element 5b. An idle roller 8 is rotatably mounted about pivot P' by means of roller bearings 6, 7. The roller 8 comprises two cylindrical, co-axial parts or elements 8a, 8b, the element 8a having a larger diameter than element 8b. Similarly, a pivot P'' extends between the arms of the element 5c. An idle roller 11 is rotatably mounted about pivot P'' by means of roller bearings 9, 10. The roller 11 comprises two cylindrical, co-axial parts or elements 11a, 11b, the element 11a having larger diameter than element 11b. The rollers 8, 11 are mounted in their respective clevis-shaped elements in such a way that the cylindrical elements of larger diameter are arranged at opposite ends of the rotor, for the reason which will be explained hereinbelow.

The position of elements 5b, 5c and their rollers relative to the central body 5a can be varied by means of slide couplings 12, 13 and accurately adjusted by means of micrometer worm screws 14, 15. The securing screws 16, 17 fasten the clevis-shaped elements 5b, 5c in any desired position. By means of the above-mentioned slide couplings, the roller 8, 11 can be displaced laterally relative to the longitudinal axis of the pump and at right angles to the radial axis a—a of rotor 5. The rollers 8, 11 with their pivots P', P" can also be displaced parallel to the axis a—a of rotor 5, by providing in the clevis-shaped elements suitable slots for accommodating a micrometer regulation unit, as already known in the art, not shown in the drawing for the sake of simplicity.

Inside the semi-cylindrical seating, conforming to the profile thereof and arranged between rollers 8, 11 and the semi-cylindrical seating, there is a pair of collapsible tubings 18, 19 made of any suitable inert material endowed with sufficient elasticity (e.g. polyvvynilchloride) in which the fluid(s) to be pumped is conveyed. The tubings are arranged substantially parallel to each other and so as to extend in the general circumferential direction.

As clearly shown in FIG. 2, a gap exists between the semi-cylindrical seating and the side surfaces of the cylindrical elements having different diameters forming the rollers, and the gap is such that only the tubing arranged between the semi-cylindrical seating and the cylindrical element having larger of that roller which at a given moment is travelling parallel to the surface of the semi-cylindrical seating, is compressed with attendant pumping action on the fluid contained therein, while in the meantime the other tubing is merely supported by the elements having smaller diameter, which therefore does not exert any appreciable flattening action on this latter tubing. No pumping action is brought about in the latter tubing by this slight flattening.

The functioning of the pump is as follow: as rotor 5 rotates in the direction shown by the arrow in FIG. 1, the cylindrical element 8a having larger diameter flattens tubing 18 (FIG. 2) against the wall of the semi-cylindrical seating, whilst the cylindrical element 8b having smaller diameter does not exert any singificant compressive action on tubing 19. This situation lasts for the whole time necessary for roller 8 to travel along the path parallel to the semi-cylindrical seating wall (i.e. until roller 8 has rotated through 180° with respect to the position shown in FIG. 1).

At this very moment, roller 11 which, during the rotation through 180° with respect to the position shown in FIG. 1, has not exerted any compressive action on any of the tubings, by means of the cylindrical element 11a having larger diameter starts to compress the tubing 19, whilst its cylindrical element 11b having smaller diameter does not exert any significant compressive action on tubing 18. From the foregoing it is apparent that during a complete rotation of rotor 5 the tubings are alternatively engaged and compressed, sufficiently to produce a pumping action, by only one of the rollers, each one for the duration of a half-rotation of the rotor 5, thereby bringing about the alternate pumping on the fluid contained in the tubings.

With reference to FIGS. 3 and 4, by means of the pump head described hereinbefore, it is possible to obtain a desired phase displacement (a delay or alternatively an advance) between the beginning of the pumping phase on one of the tubings with respect to the end of the pumping phase on the other tubing. For instance, when it is desired that the beginning of the pumping phase on one tubing coincides with the end of the pumping phase on the other tubing, after having loosened the screws 16, 17, one will set the micrometer screws 14, 15 in such a way that the clevis-shaped elements 5b, 5c be brought in the position shown very diagrammatically in FIG. 3.

From FIG. 4, which very diagrammatically illustrates the pump head shown in FIG. 1 but in a slightly different position of the rotor 5, it is apparent that when roller 8 (in the higher position) begins compression of tubing 18, roller 11 (in the lower position) has not yet completed compression of tubing 19. According to the arrangement of the clevis-shaped elements shown in FIG. 4, there is therefore a time interval during which a simultaneous compression is exerted on both tubings. Any average skilled worker will be able to set the clevis-shaped elements 5b, 5c at that relative distance which is necessary to cause any desired advance or delay between the pumping phases.

Thus, with the pump described herein, it is possible during a half-cycle to carry out the pumping on the first tubing only, whilst during the next half-cycle the pumping is carried out on the second tubing only, or alternatively it is possible to bring about a delay or advance, variable within wide limits, between the end of pumping on one tubing and the beginning of pumping on the other tubing.

What is claimed is:

1. A rotary roller pump for carrying out sequential pumping of fluid in a plurality of separate squeezable tubings, the pump comprising a plurality of tubings; a stator, having an inwardly facing seating and a rotor which is provided at opposite lateral ends with respective rollers, for engagement with the said tubings; a gap provided between said rotor and said inwardly facing seating of said stator, which seating partially surrounds said rotor, for accommodating said tubings which are arranged substantially parallel to each other and extend in a general circumferential direction; and wherein each said roller includes two cylindrical and coaxial parts having different diameters, each said cylindrical part having the larger diameter being engageable with a respective one of said tubings between that cylindrical part of larger diameter and the inwardly facing seating for exerting a pumping action on that tubing when said rotor rotates, and that each said cylindrical part having the smaller diameter being in supportive and non-pumping engagement with a different one of said tubings, which is adjacent that one engaged by said cylindrical part of larger diameter, the repsective positions of said rollers being reversed so that each of said tubings is engaged with a respective one of said cylindrical parts of larger diameter and a respective one of said parts of smaller diameter forming part of a different one of said rollers.

2. A pump according to claim 1, wherein said plurality of tubings comprise a pair of separate squeezable tubings, and wherein only two of said rollers are provided, said two rollers being in engagement with their respective tubings during respective half-rotation of the rotor whereby alternate pumping of fluid in the pair of tubings is effected.

3. A pump according to claim 1, further comprising means for micrometrically adjusting said gap between said seating and said rollers.

4. A pump according to claim 3, further comprising means for varying the time period elapsing between an end of a pumping action on one of said tubings and a beginning of a pumping action on another of said tubings.

5. A pump according to claim 4, wherein said pump has a longitudinal axis, and said means for varying the time period comprise means for enabling said rollers to be displaced laterally relative to said longitudinal axis of the pump and at right angles to a radial axis of said rotor.

6. A pump according to claim 5, wherein said rotor comprises a central body, fixedly secured to a shaft, and a pair of clevis-shaped elements removably engaged in said central body, said means for enablign said rollers to be displaced include a slide means between each said clevis-shaped element and securing screws for adjusting the relative position of said rollers and for clamping said rollers in desired position.

7. A pump according to claim 1, wherein each of said tubings are of substantially equal inner diameter.

* * * * *